US00PP31717P3

(12) United States Plant Patent
Cain

(10) Patent No.: US PP31,717 P3
(45) Date of Patent: May 5, 2020

(54) GRAPEVINE NAMED 'IFG TWENTY-FIVE'

(50) Latin Name: *Vitis vinifera*
Varietal Denomination: IFG Twenty-five

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 67 days.

(21) Appl. No.: 15/530,143

(22) Filed: Dec. 7, 2016

(65) Prior Publication Data

US 2018/0160588 P1 Jun. 7, 2018

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/0812
See application file for complete search history.

*Primary Examiner* — Kent L Bell

(57) ABSTRACT

This invention is a new and distinct grapevine variety denominated 'IFG Twenty-five'. The new grapevine is characterized by producing small to medium size elliptic full black berries having medium firm texture with a neutral flavor and which ripen in early season. Berries are borne on medium size clusters which are slightly compact and may require gibberellin applications to thin clusters and size berries.

1 Drawing Sheet

Latin name of the genus and species claimed: *Vitis vinifera.*

Variety denomination: 'IFG Twenty-five'.

BACKGROUND OF THE INVENTION

The new and distinct grapevine described and claimed herein originated from a hand pollinated cross of IFG 01073-094-195, an unnamed seedless selection from the IFG breeding program and the 01161-Bulk hybridized in May 2007. The abortive seed traces were subsequently embryo cultured and the resulting 14 plants were planted in the field in April 2006. The present variety of grapevine was selected as a single plant in June 2008 and was first asexually propagated by hardwood cuttings in December 2008 near Delano, Kern County, Calif. The resulting propagules were planted during April 2009 near Delano, Kern County, Calif. and were found to reproduce true-to-type through at least two generations of asexual reproduction.

BRIEF SUMMARY OF THE INVENTION

The new grapevine 'IFG Twenty-five' is characterized by producing small to medium size elliptic full black berries having medium firm texture with a neutral flavor and which ripen in early season. Berries are borne on medium size clusters which are slightly compact and may require gibberellin applications to thin clusters and size berries. Berries color very well. Berries store well and retain their condition for up to eight weeks in cold storage. Fruit can also be dried to make excellent quality raisins which are larger and darker colored than raisins of the 'Thompson seedless' variety (unpatented). To the inventor's knowledge, the known variety to which the new grapevine variety is most similar is the 'Beauty Seedless' variety (unpatented). 'IFG Twenty-five' differs from the 'Beauty Seedless' by having larger berry size, firmer berries, stronger thicker stems with stronger berry attachment and longer storage ability.

'IFG Twenty-five' differs from its maternal parent the 01073-094-195 by ripening approximately one month earlier, having a more elliptic berry shape and having a more full black color. The exact pollen parent of 'IFG Twenty-five' is unknown because a composite of several similar black skinned selections from the 01161 progeny were bulked together and used to pollinate the 01073-094-195. The 'IFG Twenty-five' can be distinguished from any of the selections in the bulked pollen by ripening much earlier and having, smaller abortive seed traces.

BRIEF DESCRIPTION OF THE DRAWING

The accompanying photographic drawing in FIG. 1 illustrates in full color 'IFG Twenty-five'. The photograph was taken outdoors with indirect lighting. The colors are as nearly true as is reasonably possible in a color representation of this type. The left side of the drawing has a young shoot tip with tendrils and young leaves. A mature fruit cluster is represented in the center of the drawing along with a typical berry in cross section. A mature leaf can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twenty-five' plants grown in the vicinity of Delano, Kern County, Calif. during 2013 and 2014, and is believed to apply to plants of the variety grown under similar conditions of soil and climate elsewhere:

VINE

General:

*Vigor*.—Vigorous.
*Density of foliage*.—Dense.
*Productivity*.—Productive, producing about 17 to 24 kg of marketable fruit per vine.
*Root stock*.—Own root.
*Training method*.—Typically cane pruned leaving five to seven 16-bud canes.

Trunk:

*Trunk diameter of* 4-*year-old vines at* 30 *cm above the soil line*.—About 6.8 cm.
*Shape*.—Somewhat stocky.
*Straps*.—Long, continuous.
*Surface texture*.—Smooth.
*Inner bark color*.—The following colors were observed: Greyed-orange: 166A and 166B and 166C and 165A.

SHOOTS

Young shoot:

*Form of tip*.—Wide open.
*Distribution of anthocyanin coloration on tip*.—Absent.
*Intensity of anthocyanin coloration on tip*.—Absent.
*Density of prostrate hairs on tip*.—Sparse to medium.
*Density of erect hairs on tip*.—Absent.
*Color*.—Yellow-green: 144A.

Woody shoot (mature canes):

*Internode length*.—Medium; About 12.6 cm.
*Width at node*.—About 1.4 cm.
*Cross section*.—Elliptic.
*Surface*.—Striate.
*Main color*.—The following colors were observed: Greyed-orange: 166A and 166B and 166C and 166D, and 165A and 165B.
*Density of erect hairs on nodes*.—None.
*Density of erect hairs on internodes*.—None.
*Axillary shoot length at full bloom*.—Short; Approximately 4.5 cm.

Flowering shoot:

*Vigor during flowering*.—Medium.
*Attitude during flowering on shoots not tied*.—Semi-erect.
*Color*.—Dorsal side of internodes — Yellow-green: 146C, with a few Red-purple stripes: 59B.
*Color*.—Ventral side of internodes — Yellow-green: 146C.
*Color*.—Dorsal side of nodes — Yellow-green: 146C, with Red-purple stripes: 59B.
*Color*.—Ventral side of nodes — Yellow-green: 146C.
*Density of prostrate hairs on nodes*.—Very sparse.
*Density of erect hairs on nodes*.—None.
*Density of prostrate hairs on internode*.—None to very sparse.
*Density of erect hairs on internode*.—None.
*Anthocyanin coloration of buds*.—Absent.

Tendrils:

*Distribution on the shoot* (*at full flowering*).—Discontinuous.
*Length of tendril*.—Very long; About 32.5 cm.
*Thickness of tendril* 2 *cm from base*.—About 2.1 mm.
*Color*.—The following colors were observed: Yellow-green: N144A and 151A.
*Form*.—Trifurcated and quadfurcated.
*Number of consecutive tendrils*.—2.

LEAVES

Young leaves:

*Color of upper surface of first four distal unfolded leaves*.—The following colors were observed: Yellow-green: 146C and Greyed-red: 178B and 178C.
*Color of young leaf lower surface*.—The following colors were observed: Yellow-green: 146B and Greyed-orange: 176B.
*Average intensity of anthocyanin coloration of six distal leaves prior to flowering*.—Medium.
*Density of prostrate hairs between veins* (*lower surface*).—Absent to very sparse.
*Density of prostrate hairs on veins* (*lower surface*).—Sparse.
*Density of erect hairs between veins* (*lower surface*).—Medium.
*Density of erect hairs on veins* (*lower surface*).—Medium.

Mature leaves:

*Average length*.—About 13.2 cm.
*Average width*.—About 17.6 cm.
*Mature leaf size*.—Medium to large.
*Shape of blade*.—Wedge-shaped.
*Number of lobes*.—5.
*Blade venation*.—Palmate.
*Anthocyanin coloration of main veins on upper side of blade*.—Weak.
*Mature leaf profile*.—Undulate.
*Blistering surface of blade upper surface*.—Very weak.
*Leaf blade tip*.—Curved downwardly.
*Undulation of margin*.—Medium.
*Undulation of blade between main and lateral veins*.—Overall.
*Shape of teeth*.—Both sides concave.
*Length of teeth*.—Medium to long.
*Ratio length/width of teeth*.—Medium.
*Shape of upper lateral sinuses*.—Lobes slightly overlapping.
*Depth of upper lateral sinuses*.—Shallow to medium.
*General shape petiole sinus*.—Half open to lobes slightly overlapping.
*Shape of base of upper leaf sinuses*.—V-shaped.
*Tooth at petiole sinus*.—Absent.
*Density of prostrate hairs between veins on lower surface of blade*.—Very sparse.
*Density of erect hairs between veins on lower surface of blade*.—Medium.

*Density of prostrate hairs on main veins on lower surface of blade*.—Very sparse.
*Density of erect hairs on main veins on lower surface of blade*.—Medium.
*Density of prostrate hairs on main veins on upper surface of blade*.—Sparse.
*Density of erect hairs on main veins on upper surface of blade*.—None.
*Autumn coloration of leaves*.—Leaves can be a single color or a combination of colors, in a mottled pattern or on the edges of the leaves. The following colors were observed: Greyed-purple: 187A and 187B and 187C, and 184A and 184B and 184C and 184D, and Greyed-yellow: 161C and 161D.

Upper surface:
*Color*.—Yellow-green: 146A.
*Color of main veins*.—Yellow-green: 145B.
*Anthocyanin coloration of main veins*.—Absent to very weak.
*Surface appearance*.—Semi-glossy to dull.
*Blistering surface of blade*.—Weak.

Lower surface:
*Color*.—Yellow-green: 146A.
*Color of main veins*.—Yellow-green: 145C.
*Anthocyanin coloration of main veins* (*lower surface*).—Weak.
*Glossiness*.—Weak.
*Surface texture*.—Smooth.
*Surface appearance*.—Dull.

Petiole:
*Length*.—About 11.9 cm.
*Length of petiole compared to middle vein*.—Slightly shorter.
*Diameter of petiole* 2 *cm from blade*.—About 4.5 mm.
*Color of petiole*.—The following colors were observed: Yellow-green: 145C and Greyed-red: 182B.
*Density of prostrate hairs on petiole*.—Very sparse.
*Density of erect hairs on petiole*.—None.

Buds:
*Bud fruitfulness*.—Basal: Mostly fruitful.
*Dormant bud length*.—About 5.7 mm.
*Dormant bud width in the proximal/distal plane*.—About 6.6 mm.
*Dormant bud color*.—Greyed-orange: 166B.
*Position of first fruitful shoot on previous season cane*.—$1^{st}$ to $2^{nd}$ node.
*Time of bud burst*.—Mid to late season; About Mar. 13, 2013.

FLOWERS

General:
*Flower sex*.—Hermaphrodite.
*Length of single flower, unopened*.—About 3.3 mm.
*Width of single flower*.—Unopened: About 2.2 mm, opened: About 6.1 mm.
*Stamen length*.—About 2.9 mm.
*Stamen count*.—5 to 6.
*Pollen color*.—Yellow: 10B.
*Pollen amount*.—Moderate.
*Pistil length*.—About 2.9 mm.
*Pistil color*.—Yellow-green: 144A.
*Length of first inflorescence*.—Medium: About 17.7 cm long by 8.4 cm wide.
*Position of first flowering and fruiting node*.—$3^{rd}$ to $4^{th}$ (current season growth).
*Number of inflorescence per flowering shoot*.—1.1 to 2; About 1.9.
*Time of bloom*.—Late as compared with similar varieties in the growing area of Delano, Calif.
*Date of full bloom*.—About May 3, 2014.

FRUIT

General:
*Ripening period*.—Early: Approximately Jul. 19, 2013.
*Use*.—Fresh market and dried.
*Keeping quality*.—Good, remains commercially acceptable when stored up to 8 weeks at 0° C. and high relative humidity.
*Resistance to*.—Insects: Average typical of *Vitis vinifera* species. Diseases: Average typical of *Vitis vinifera* species.
*Refractometer test*.—Soluble solids: About 21.6 Brix.
*Brix/acid*.—About 49.1.
*Titratable acidity*.—About 0.44.
*Juice ph*.—About 3.72.

Cluster:
*Mature cluster length* (*peduncle excluded*).—About 26.0 cm.
*Mature cluster width*.—About 15.0 cm.
*Mature cluster weight*.—About 495 g.
*Bunch density*.—Medium.
*Number of berries*.—About 150.
*Form*.—Conical.

Peduncle:
*Lignification of peduncle*.—Medium.
*Length of peduncle*.—Medium: approximately 4.5 cm.
*Width of peduncle*.—About 8 mm.
*Color of peduncle*.—Yellow-green: 146C.

Berry:
*Uniformity of size*.—Uniform.
*Single berry weight*.—About 3.4 g natural; to about 6.6 g when treated with gibberellic acid.
*Shape*.—Elliptic.
*Seeds*.—Absent.
*Cross section*.—Circular.
*Berry dimensions*.—Longitudinal axis: about 2.1 cm. Horizontal axis: about 1.6 cm.
*Pedicel length*.—About 5.5 mm.
*Pedicel width*.—About 2.0 mm.
*Pedicel color*.—Yellow-green: 146D.
*Berry firmness*.—Medium.
*Particular flavor*.—Neutral.
*Bloom* (*cuticular wax*).—Medium.
*Berry separation from pedicel*.—Medium to difficult.
*Skin color* (*without bloom*).—Greyed-purple: N186A.
*Berry flesh color*.—Greyed-purple: N187D.

Skin:
*Thickness*.—Thick.
*Skin toughness*.—not notable when chewing.
*Reticulation*.—Absent.
*Tenacity*.—Tenacious to flesh.

What is claimed:

1. A new and distinct variety of grapevine as herein illustrated and described.

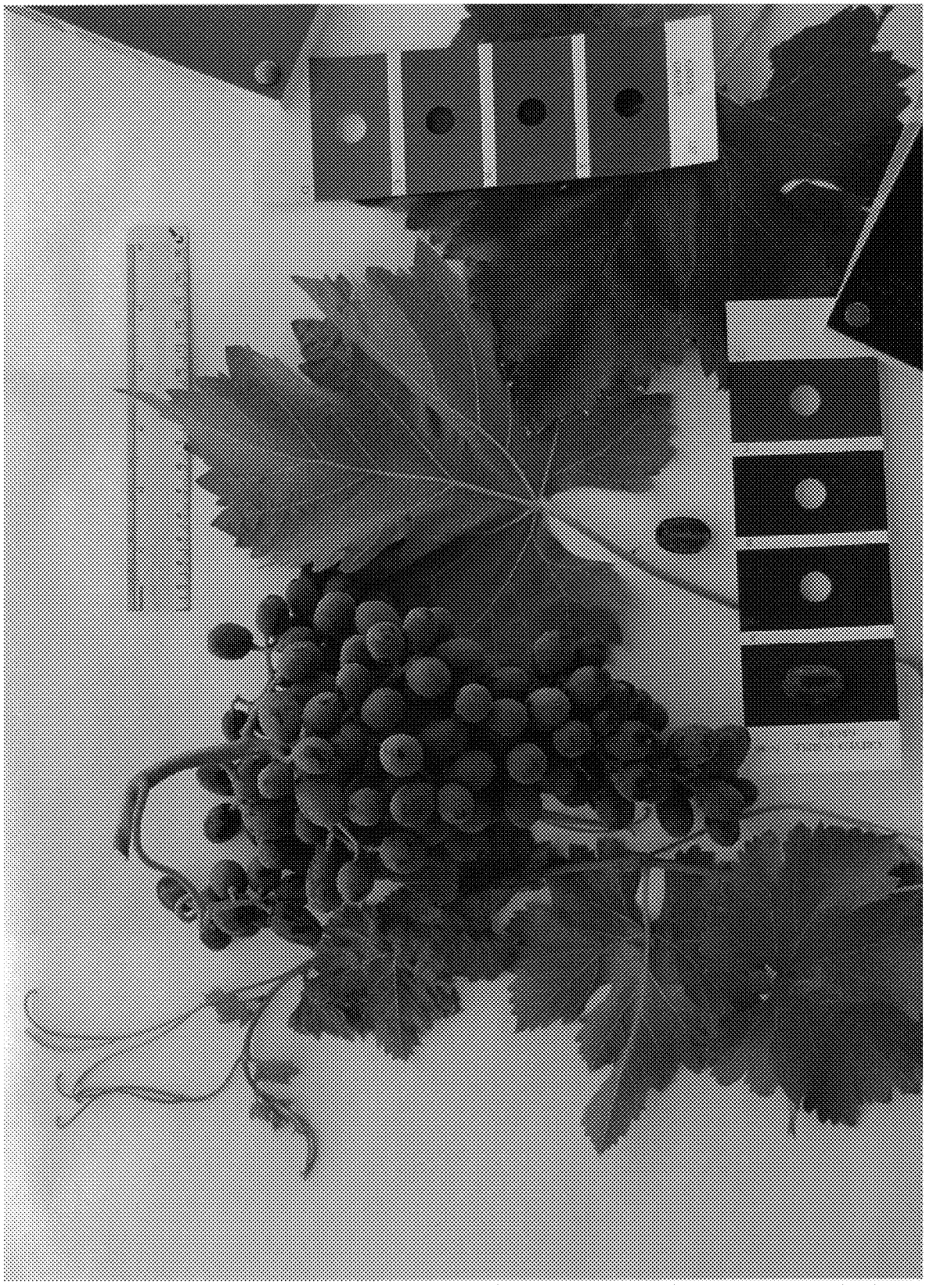

* * * * *